United States Patent
Jelfs et al.

(10) Patent No.: US 10,682,082 B2
(45) Date of Patent: *Jun. 16, 2020

(54) SENSOR SYSTEM AND METHOD WHICH MAKES USE OF MULTIPLE PPG SENSORS

(71) Applicant: KONINKLIJKE PHILIPS N.V., Eindhoven (NL)

(72) Inventors: Sam Martin Jelfs, Riethoven (NL); Jozef Hubertus Gelissen, Herten (NL); Reinder Haakma, Eindhoven (NL); Laurentia Johanna Huijbregts, Eindhoven (NL); Adrianus Petrus Johanna Maria Rommers, Veldhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 186 days.

This patent is subject to a terminal disclaimer.

(21) Appl. No.: 15/578,791

(22) PCT Filed: Jun. 22, 2016

(86) PCT No.: PCT/EP2016/064329
§ 371 (c)(1),
(2) Date: Dec. 1, 2017

(87) PCT Pub. No.: WO2017/001250
PCT Pub. Date: Jan. 5, 2017

(65) Prior Publication Data
US 2018/0177440 A1 Jun. 28, 2018

(30) Foreign Application Priority Data
Jun. 30, 2015 (EP) ..................................... 15174451

(51) Int. Cl.
*A61B 5/00* (2006.01)
*A61B 5/1495* (2006.01)
(Continued)

(52) U.S. Cl.
CPC .......... *A61B 5/1495* (2013.01); *A61B 5/0015* (2013.01); *A61B 5/02427* (2013.01);
(Continued)

(58) Field of Classification Search
CPC ....... A61B 5/024; A61B 5/00; A61B 5/14552; A61B 5/02427; A61B 5/14455;
(Continued)

(56) References Cited

U.S. PATENT DOCUMENTS

| 8,140,143 B2 | 3/2012 | Picard et al. |
| 2005/0192488 A1 | 9/2005 | Bryenton et al. |

(Continued)

FOREIGN PATENT DOCUMENTS

| WO | 2013156461 A1 | 10/2013 |
| WO | 2013167026 A2 | 10/2013 |

(Continued)

OTHER PUBLICATIONS

Kim, et al., "Relationship between blood pressure parameters and pulse wave velocity in normotensive and hypertensive subjects: invasive study" Journal of Human Hypertension (2007), 21, pp. 141-148.

*Primary Examiner* — Eric J Messersmith (57) ABSTRACT

A sensor system comprises first and second PPG sensors. A monitoring system monitors detection by at least one of the first and second detectors an optical calibration signals, for performing time calibration between the first and second PPG sensors. This system makes use of two PPG sensors. To enable these sensors to be independent units, rather than being fully integrated into a combined system, a calibration (Continued)

system is provided. Based on detected optical signals, the behavior over time of each PPG sensor can be monitored and thus calibration can take place.

10 Claims, 6 Drawing Sheets

(51) Int. Cl.
*A61B 5/1455* (2006.01)
*A61B 5/024* (2006.01)

(52) U.S. Cl.
CPC ........ *A61B 5/1455* (2013.01); *A61B 5/14552* (2013.01); *A61B 2560/0233* (2013.01); *A61B 2560/0456* (2013.01); *A61B 2562/0242* (2013.01); *A61B 2562/04* (2013.01); *A61B 2562/146* (2013.01)

(58) Field of Classification Search
CPC ................ A61B 5/1495; A61B 5/0015; A61B 2560/0456; A61B 2562/0242; A61B 2562/146; A61B 2560/0233; A61B 2562/04

See application file for complete search history.

(56) References Cited

U.S. PATENT DOCUMENTS

| | | |
|---|---|---|
| 2008/0214936 A1 | 9/2008 | Wiering et al. |
| 2012/0053432 A1 | 3/2012 | Huiku et al. |
| 2014/0275888 A1 | 9/2014 | Wegerich et al. |
| 2017/0143267 A1* | 5/2017 | Kovacs ................ A61B 5/6887 |
| 2019/0254524 A1* | 8/2019 | Granqvist ............ A61B 5/0024 |

FOREIGN PATENT DOCUMENTS

| | | |
|---|---|---|
| WO | 2013166461 A1 | 11/2013 |
| WO | 20140124520 A1 | 8/2014 |

* cited by examiner

SENSOR SYSTEM AND METHOD WHICH MAKES USE OF MULTIPLE PPG SENSORS

This application is the U.S. National Phase application under 35 U.S.C. § 371 of International Application No. PCT/EP2016/064329, filed on Jun. 22, 2016, which claims the benefit of European Application Serial No. 15174451.3, filed Jun. 30, 2015. These applications are hereby incorporated by reference herein.

FIELD OF THE INVENTION

The present invention relates to the field of PPG sensors, and in particular a sensor system and method which makes use of multiple PPG sensors. In particular, the invention relates to determining the pulse delay arising in a patient using multiple PPG sensors.

BACKGROUND OF THE INVENTION

The pulse wave velocity (PWV) is the speed at which a pulse travels within the arteries. It is known that PWV is a measure of arterial stiffness and also correlates with blood pressure (either Mean Arterial Pressure (MAP), or Pulse Pressure (PP)). The PWV can be calculated from the pulse transit time (PTT; the time it takes for a blood pulse to travel from the heart to a certain location), or more generally from the pulse delay (PD; the difference in PTT of two different locations on the body). PD and PTT are interchangeable for the purposes of this description, and they each may be used to provide indications in respect of PWV. The pulse delay is the difference between two Pulse Transit Times at different locations on the body originating from the same heartbeat.

Typically PWV measures are made either invasively using a catheter probe, or on the skin using tonometry. By measuring the time difference between the pulse arriving at one location on the body (such as the upper arm) and another location (such as the wrist), the velocity can be determined.

One non-invasive way to do this measurement would be to use photoplethysmograph (PPG) sensors. These measure volumetric changes of a body.

A pulse oximeter is a common example of a PPG-based sensor. The purpose of pulse oximetry is to monitor the oxygen saturation of a patient's blood. While the purpose of such a sensor is to obtain a measure of blood oxygen saturation, it also detects changes in blood volume in the skin, and thereby performs PPG sensing. By detecting changes in blood volume, a cyclic signal corresponding to the pulse is obtained. PPG sensors, such as pulse oximeters, are thus commonly used to provide a measure of the pulse rate.

A PPG sensor contains at least one LED, and one light sensor. The LED and sensor are placed such that the LED directs light into the skin of the user, which is reflected or transmitted, and detected by the sensor. The amount of reflected/transmitted light is determined by, amongst others, the perfusion of blood within the skin.

The PPG system for example includes a red LED, a near-infrared LED, and a photodetector diode. The sensor is typically configured with the LEDs and photodetector diode directly on the skin of the patient, typically on a digit (finger or toe) or earlobe.

Other places on the patient may also be suitable, including the forehead, the nose or other parts of the face, the wrist, the chest, the nasal septum, the alar wings, the ear canal, and/or the inside of the mouth, such as the cheek or the tongue.

The LEDs emit light at different wavelengths, which light is diffused through the vascular bed of the patient's skin and received by the photodetector diode. The changing absorbance at each of the wavelengths is measured, allowing the sensor to determine the absorbance due to the pulsing arterial blood alone, excluding venous blood, skin, bone, muscle, and fat for example. The resulting PPG signal may then be analyzed.

Other simpler versions of a system for obtaining PPG data may be used, including a version with a single light source of one or more wavelengths. The absorption or reflectance of the light is modulated by the pulsatile arterial blood volume and detected using a photodetector device.

In transmissive pulse oximetry, a sensor device is placed on a thin part of the patient's body. Reflectance pulse oximetry may be used as an alternative to transmissive pulse oximetry. This method does not require a thin section of the person's body and is therefore well suited to more universal application such as the feet, forehead and chest.

A basic design of a PPG sensor for example has a certain light output frequency (e.g. 128 Hz) with which the light source is pulsed. A sampling frequency of the optical sensor is higher, for example 256 Hz so that it measures during light source activation and between light source activations. This allows the system to distinguish between the emitted light from the LED and the ambient light, and thereby filter out the ambient light from the signal received during a light source pulse.

In other known proposals, PPG data can be obtained from camera images, where ambient light and/or additional light sources are used to illuminate the tissue, such as skin. PPG measurements can thus even be carried out at a distance from the tissue, where the light source and/or detector are not in contact with the tissue, such as in the case of camera-based measurements.

The PPG data may be obtained at one or more wavelengths, such as any number of wavelengths typically between 1 and 10, but more than 10 wavelengths may even be used.

Apparatus and techniques for obtaining PPG data, such as pulse oximetry data, are well known in the art and indeed many different PPG sensors are commercially available. They are for example used in devices for measuring heart rate during exercise.

This known technology could be used to measure PD. Known devices have the ability to measure and log the PPG signal for a given period of time, after which the data can be downloaded from the device, and analyzed to calculate the PD.

One limitation of these devices for the calculating PD is that it would require two units located at a distance apart on the body.

One problem that arises is the need to ensure accurate time synchronization between the two devices. Typically the internal clocks of the logging devices (i.e. the clocks used to link the output data with an actual time at which the data was recorded) are either set manually by the user, or from a computer when configuring/downloading data from the devices. The limitation of this is that if manually set the clocks are for example only accurate to the minute level, and to the second level when set via a computer. For accurate PD measurements, it is necessary to tell the time of arrival of the pulse wave to the millisecond level of accuracy. In order to attain this level of accuracy there is a need for precise synchronization between the two PPG devices.

When two PPG devices have independent clocks, they will inevitably drift relative to each other. To enable standard and independent PPG sensors to be used, the desired solution would not require electrical communication between the devices. They are for example independently started using their own on/off button. It is of course impossible in practice to manually start both devices at exactly the same time. Furthermore, it is desirable to avoid having any unnecessary processes running on the PPG devices.

While synchronization would be possible using a fully integrated system (for example based on a microprocessor clock), there is a need for a solution which enables the use of independent PPG sensors together to enable multiple synchronized measurements, for example for PD measurement.

SUMMARY OF THE INVENTION

Examples in accordance with a first aspect of the invention provide a sensor system, comprising:

a first PPG sensor having a first light source and a first optical detector;

a second PPG sensor having a second light source and a second optical detector;

a docking station, which provides a first optical coupling between the first light source and the first optical detector and a second optical coupling between the second light source and the second optical detector;

a monitoring system adapted to monitor detection of first and second optical calibration signals, wherein the first optical calibration signal is adapted to be detected by the first optical detector of the the first PPG sensor and is generated by the first optical coupling and the second optical calibration signal is adapted to be detected by the second optical detector of the second PPG sensor and is generated by the second optical coupling, wherein the monitoring system is adapted to perform time calibration between the first and second PPG sensors.

The calibration signals are "generated" by the optical couplings. This may involve a light modulation function of light that has been output by the first and second light sources, for example a reflection or absorption function. Thus, the light may originally be generated by the PPG sensors, but only after modulation by the optical couplings are the calibration signals formed.

The PPG sensors are for example reflective PPG sensors.

This system makes use of two PPG sensors. To enable these sensors to be independent units, rather than being fully integrated into a combined system, a monitoring system is provided for providing time calibration. Based on detection of signals using at least one of the PPG sensors which include some known absolute timing information, the behavior over time of each PPG sensor can be monitored and thus calibration can take place.

The timing calibration may take place in real time, or else it may be carried out as part of the analysis of two sets of stored PPG sensor logged data.

The individual PPG sensors may provide continuous monitoring without reference to any particular external time reference. When such sensors are designed for example for pulse rate monitoring or for blood oxygen measurement over time, there is no need for great accuracy with respect to any external timing reference. Instead, the time at which data is recorded is simply linked to an internal clock.

The monitoring system is for monitoring detection of first and second optical calibration signals.

The first optical calibration signal is generated by the first light source and the second optical calibration signal is generated by the second light source, and the system comprises a docking station, which provides a first optical coupling between the first light source and the first optical detector and a second optical coupling between the second light source and the second optical detector.

The detector of one PPG sensor is used to detect the light output from the light source of that same PPG sensor.

Preferably, the first and second optical couplings have an optical function with synchronized time dependency. In this way, if the nature of the optical function can be determined from the detected signal, then absolute timing information can then be allocated to the detected signal. This enables relative timing information between the two PPG sensor outputs to be obtained when they are subsequently used. The first and second optical couplings may comprise a reflector with a reflection characteristic which is varied over time. A known optical path between the light source and detector then includes this time-varying reflection characteristic.

In an alternative set of examples, the first optical calibration signal for detection by the first PPG sensor is generated by the second light source and the second optical calibration signal for detection by the second PPG sensor is generated by the first light source.

In this way, calibration measurements take place with the first light source optically coupled to the second optical detector and with the second light source optically coupled to the first optical detector.

In this case, there is an optical path between the light source of one PPG sensor and the detector of the other PPG sensor. By way of example, the first light source may send a recognizable signal to the second detector, which then returns it (after a known delay) using the second light source back to the first detector. By analyzing the detected signals, and their timings in particular, time offsets can be calculated. When subsequently combining received signals from both sensors, this timing offset can then be used so that the relative absolute timing between the two PPG sensor traces is known. This relative timing then enables the pair of traces to be analyzed.

Note that no absolute time values are needed other than the known delay.

The calibration system may be adapted to perform calibration with the first and second PPG sensors positioned against each other. In this case, the optical path between the light source and the detector (of the other PPG sensor) is simply a direct optical connection.

The calibration system may again comprise a docking station, which provides a first optical coupling between the first light source and the second optical detector and a second optical coupling between the second light source and the first optical detector. The optical path between the light source and the detector (of the other PPG sensor) is again a direct optical connection, but it is implemented by a docking station rather than by coupling the PPG sensors together. The docking station may make the required alignment easier for the user to achieve. The docking station may for example comprise optical fibers for providing the first and second optical couplings or else a mirror arrangement may be used.

In another alternative set of examples, there is instead a docking station which comprises a light source for generating the first and second optical calibration signals. In this case, the optical synchronization signals are generated externally. As long as these signals are synchronized, and can be detected in the photodetector outputs, an absolute time difference can then be obtained.

The first and second PPG sensors for example each comprise pulse oximeters. These are commercially available low cost devices.

Examples in accordance with another aspect of the invention provides a pulse delay measurement device, comprising:
- a sensor system as defined above; and
- a controller for obtaining PPG signals from the first and second PPG sensors, and deriving a pulse delay using the timing calibration.

Examples in accordance with another aspect of the invention provide a sensor calibration method for calibrating first and second PPG sensors, the first PPG sensor having a first light source and a first optical detector and the second PPG sensor having a second light source and a second optical detector, the method comprising:
- placing the first and second PPG sensors on a docking station, which provides a first optical coupling between the first light source and the first optical detector and a second optical coupling between the second light source and the second optical detector,
- generating a first optical calibration signal using the optical coupling and generating a second optical calibration signal using the second optical coupling;
- performing time calibration between the first and second PPG sensors; and
- controlling the first and second optical couplings with synchronized time dependency.

This method performs timing calibration between two PPG sensors, which may be independent units with no communication between them and therefore no synchronization between them.

There are first and second optical calibration signals each for reception by one of the PPG sensors.

The first optical calibration signal is generated using the first light source and the second optical calibration signal is generated using the second light source.

The first light source is in this way optically coupled to the first optical detector and the second light source is optically coupled to the second optical detector.

In an alternative set of examples, the first optical calibration signal may be generated using the second light source and the second optical calibration signal may be generated using the first light source.

In this case, the first light source may instead be optically coupled to the second optical detector and the second light source may instead be optically coupled to the first optical detector, wherein the optical couplings are achieved by:
- positioning the first and second PPG sensors against each other; or
- placing the first and second PPG sensors on a docking station, which provides a first optical coupling between the first light source and the second optical detector and a second optical coupling between the second light source and the first optical detector.

The invention also provides a pulse delay sensing method comprising:
- performing sensing calibration using the method as defined above; and
- after the sensing calibration, obtaining PPG signals from the first and second PPG sensors, and deriving a pulse delay. This may in turn be used to derive a PWV measure, which may be absolute or relative.

The calibration may be implemented by a computer program.

BRIEF DESCRIPTION OF THE DRAWINGS

Embodiments of the invention will be described, by way of example only, with reference to the drawings, in which.

DETAILED DESCRIPTION OF THE EMBODIMENTS

The invention provides a sensor system, comprising first and second PPG sensors. A monitoring system monitors detection by at least one of the first and second detectors of an optical calibration signal, for performing time calibration between the first and second PPG sensors.

This system makes use of two PPG sensors. To enable these sensors to be independent units, rather than being fully integrated into a combined system, a calibration system is provided. Based on detected optical signals, the behavior over time of each PPG sensor can be monitored and thus calibration can take place.

Figure 1:
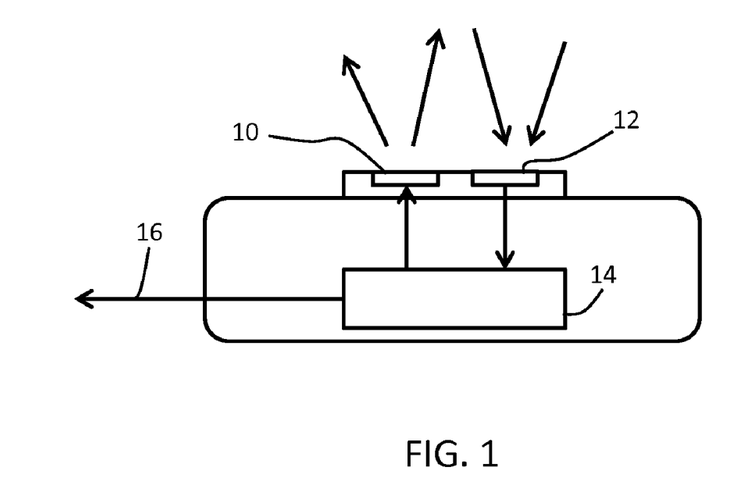
FIG. 1 shows a known PPG sensor.

FIG. 1 shows a known PPG sensor.

It comprises a light source 10 and an optical detector 12. The light source may comprise a single multi-wavelength light source, or multiple light units with different output wavelengths. The sensor has a processor 14 and it generates an output 16 in the form of a PPG signal which varies over time. The processor includes an internal clock and a memory. The output may be provided in real time and/or it may be logged and stored as a trace over time during a monitoring period. The stored trace may then be analyzed after the monitoring period is over.

The PPG sensor for example comprises a pulse oximeter. The output 16 may be interpreted to provide a pulse rate.

The invention is based on the combination of two PPG sensors which may be of the general type shown in FIG. 1.

Figure 2:
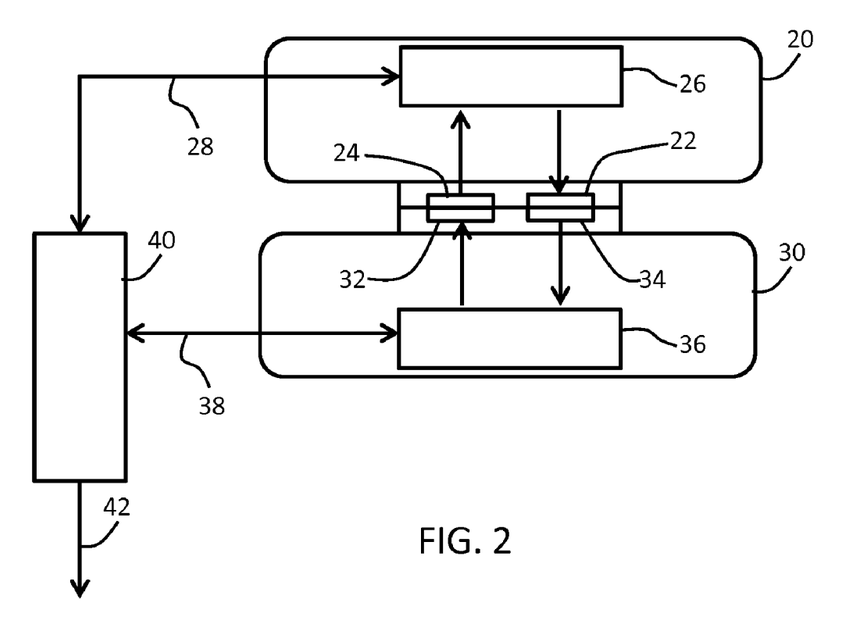
FIG. 2 shows a first example of a sensor arrangement using multiple PPG sensors.

FIG. 2 shows a first example of system to explain the principles of the synchronization approach. FIG. 2 relates to a cross coupled architecture.

A first PPG sensor 20 has a first light source 22 and a first optical detector 24.

A second PPG sensor 30 has a second light source 32 and a second optical detector 34.

Each PPG sensor has its own processor 26, 36 generating a PPG output 28, 38.

In this example, a calibration system comprises a controller 40 which is adapted to operate the first and second light sources 22, 32 at a controlled time or times. The controller 40 communicates with the processors 26, 36 as well as receiving the sensor signals.

The detection by the first and second detectors is monitored, and the optical path between each light source and its corresponding detector is known. Timing calibration is based on the monitored detection.

The version of FIG. 2 has the two PPG sensors 20, 30 mounted against each other, so that the output of the light source 22 of the first PPG sensor is fed directly to the detector 34 of the second PPG sensor, and the output of the light source 32 of the second PPG sensor is fed directly to the detector 24 of the first PPG sensor. The known optical path between each sensor-detector pair is thus a direct optical coupling.

The two optical PPG sensors may be independent units, rather than being fully integrated into a combined system. There is no timing information shared between them. Their outputs 28, 38 comprise waveforms which vary along a time axis, but the time axes of the two sensors are not synchronized.

The behavior over time of each PPG sensor can be monitored and thus calibration can take place.

In the example of FIG. 2, no additional hardware to the two PPG sensors themselves is required. The calibration controller 40 may be implemented in software.

With the devices coupled in this way a synchronization process can be triggered either by the user, or by another means.

During synchronization, one (or both) of the PPG sensors is controlled to produce a known test signal, which can later be analyzed for the time correction. This signal may take the form of a "call and response" in that the first device 20 produces a known light pattern, which is detected by the second device 30. When the second device 30 receives this pattern, it in turn produces a known pattern with a known time delay. When the data captured from the two devices is analyzed in conjunction with each other, the synchronization patterns will be evident in the signal, and the time offset can be calculated.

In this way, an optical synchronization pattern can be used to synchronize the data recordings from the two devices. This synchronization may thus be carried out after the recordings have been made, rather than in real time, or else it may be carried out in real time.

By performing a time calibration at both the beginning and the end of a data recording event, it is possible not only to correct for any offset between the two logging device clocks, but also to calculate and correct for any drift between the two clocks. Thus, synchronization can occur either within a given time period prior to a measurement taking place, after a measurement has taken place, or both.

Instead of having one controller 40 that can operate both the first light source 22 and the second light source 32, the controller 40 could also be connected to or integrated in only the first PPG sensor 20, while the other PPG sensor 30 could have its own controller or no controller at all. For example, by pressing a button on PPG sensor 20, the controller could operate the first light source 22 such that it would flash its lights in a certain pattern in time. In the signal of PPG sensor 30, which might be read out instantly or afterwards when analyzing the data, this light pattern can be recovered.

FIG. 3 shows in simplified schematic form the approach explained above, and shows time traces for the first and second light sources LS1 and LS2 and the detected signals for the first and second detectors D1 and D2.

Figure 3A:
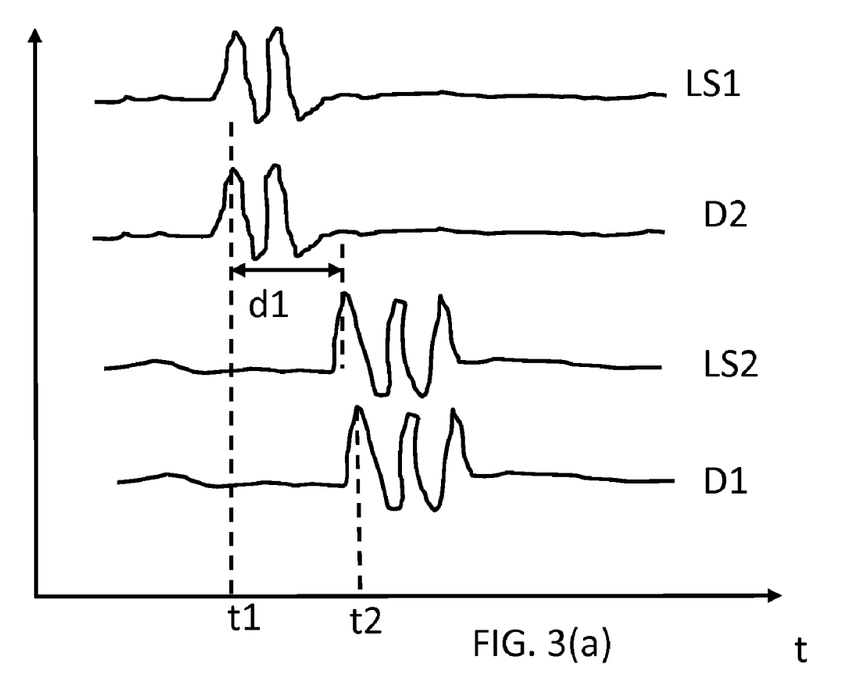
FIG. 3 is a set of timing waveforms for explaining how the timing calibration may take place.

FIG. 3(a) shows the use of an initial pulse to determine the delay between the time clocks.

A first pattern is generated by the first light source LS1. This results in a detected output from the second detector D2, and this appears in the recorded trace provided as the output of the second PPG sensor. After a known delay d1 the second PPG sensor sends a second pattern (which may in fact be the same as the first) which is received by the first detector D1. This appears in the trace recorded of the first PPG sensor.

The time delay between one light source emitting a pattern and a detector detecting it may either be negligible or else it may be taken into account when analyzing the traces.

The absolute value of the time shift between the signal D2 and D1 is thus known. In this way, if the local clocks of the two PPG sensors represent these times with an incorrect relative time shift, the timing can be calibrated. Time point t1 is on the time axis of the second PPG sensor whereas time point t2 is on the time axis of the first PPG sensor.

One or other of the traces D1 and D2 can be time shifted to make the time difference between the time points t1 and t2 equal to the delay d1 or else equal to the delay d1 plus the latency introduced between LS2 and D1 if it is relevant.

The example of FIG. 3(a) shows how the offset between two clocks can be determined based on a single synchronization action. When drift between the two clocks also needs to be determined, two (or more) synchronization actions may be performed.

Figure 3B:
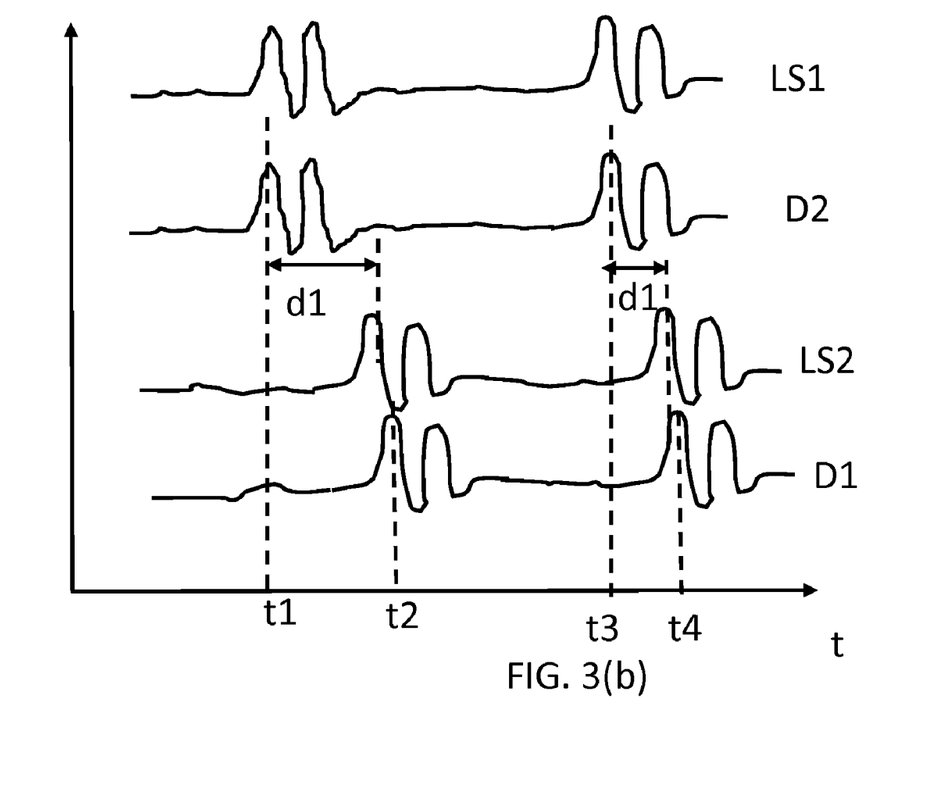

This is shown schematically in FIG. 3(b), in which the same signals are shown. This time, there is a first synchronization operation at the beginning of the device operation, and a second synchronization at the end of the device operation. The first synchronization is as described above, and the second is the same, with device actuation at time t3 and reception of the returned signal at time t4 (of the two different clock domains). The same delay d1 gives rise to a different time difference between the two clock domains (i.e. t2−t1 is different to t4−t3 even though d1 is the same). This is the result of the relative drift between the two clocks. The time delay d1 looks different at the start and end because it is a time difference as measured between two clock domains.

Figure 4:
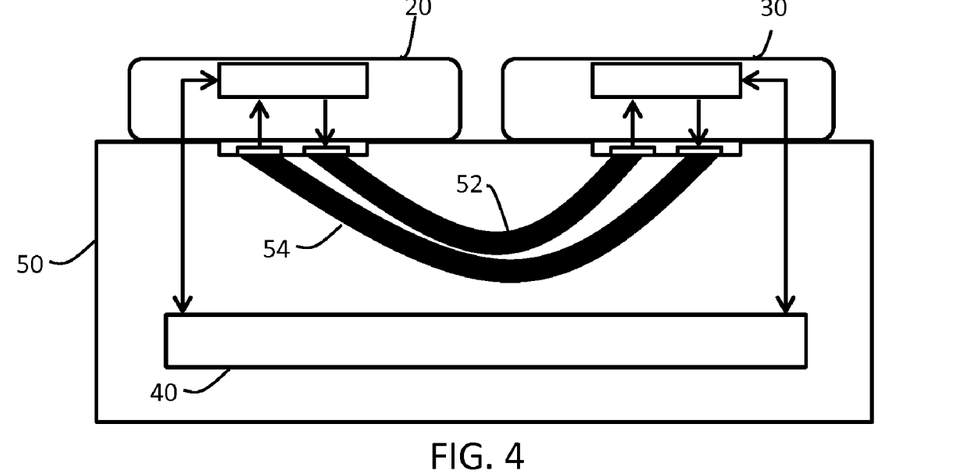
FIG. 4 shows a second example of a sensor arrangement using multiple PPG sensors.

The example of FIG. 2 above makes use of a direct coupling between the two PPG sensors, by placing them back to back. FIG. 4 shows a system which works in exactly the same way, but uses a docking station 50, which provides a first optical coupling 52 between the first light source and the second optical detector and a second optical coupling 54 between the second light source and the first optical detector. The optical path is again a direct optical connection for example using optical fibers. However, a mirror arrangement may instead be used.

Figure 5:
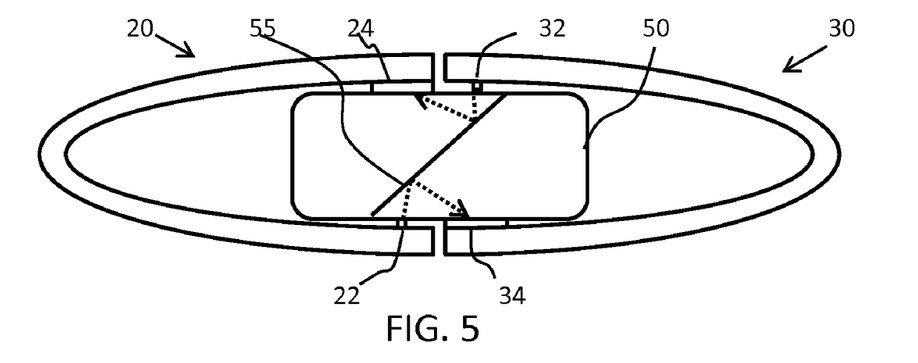
FIG. 5 shows a third example of a sensor arrangement using multiple PPG sensors.

FIG. 5 shows an example in which two transmissive PPG sensors 20, 30 such as ear clips or finger clips are used. The clips have a respective LED 22, 32 and a photodetector 24, 34 as in the examples above, but they are for mounting on opposite sides of tissue being examined. The system again comprises a passive docking station 50 on which the finger and/or ear clips 20, 30 are placed. A controller operates the light source 22 of the first sensor 20 to send a light signal. The light enters the docking station, where it is reflected by a mirror 55, after which it reaches the photodetector 34 of the second sensor 30. Similarly, the LED 32 of the second sensor 30 is optically coupled to the photodetector 24 of the first sensor 20.

Figure 6:
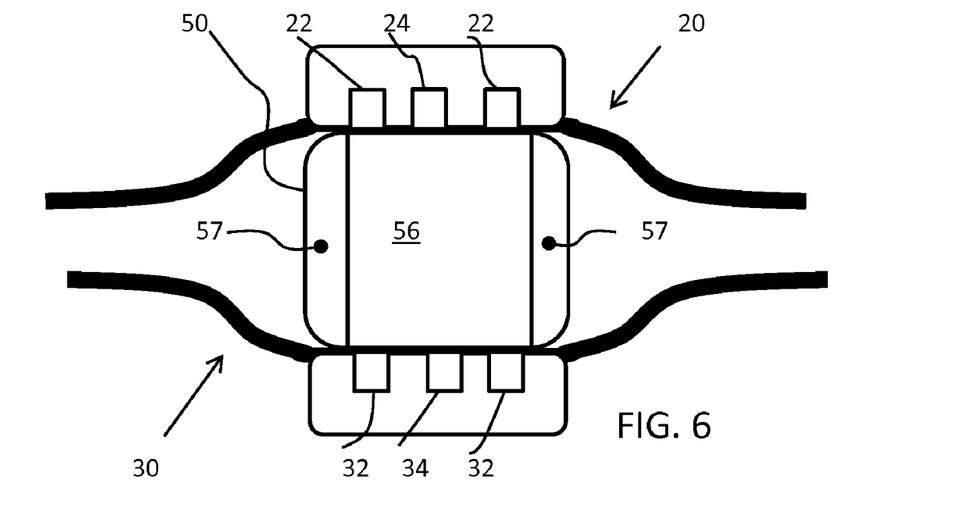
FIG. 6 shows a fourth example of a sensor arrangement using multiple PPG sensors.

FIG. 6 shows an example for reflective PPG sensors that do not have a flat surface and/or for which the light source(s) of the one sensor cannot easily be laid on top of the light detector(s) of the other as in FIG. 2. In FIG. 6, each sensor 20, 30 is in the form of a wrist watch, with the LEDs 22, 32 and photodetectors 32, 34 at the base of the watch face. In this example, each sensor has one photodetector 24, 34 in the middle and two LEDs 22, 32 on the sides.

The sensors 20, 30/ have a curved bottom plate to fit against the skin of the wrist of the user. The docking station 50 has a shape that fits the curvatures of sensors 20 and 30. It has a translucent inner part 56 and an opaque outer part 57. The opaque outer part 57 prevents ambient light entering the optical coupling between the two sensors which takes place via translucent inner part 56. The way the light signals are generated and processed is similar to the examples described above.

The examples of FIGS. 2 and 4 to 6 require the PPG sensors to send pulses at one time and to receive pulses at a later time (when the light source is turned off). This may not be possible for some most basic designs of PPG sensor. For example the sensor may only process samples received while the light source is turned on. When the light source is turned off, the device is expecting only to see ambient light. In some designs, this ambient light level is measured so that it can be filtered out from the sensor measurements when the light source is turned on. In this way, ambient light compensation is carried out by which the optical detector signal received when the light source is turned off is subtracted from the optical detector signal received when the light source is turned on. Thus, the examples above are suitable for certain types of PPG sensor only, in which there is for example continuous monitoring of the received light signal.

Optionally, as soon as the optical calibration signal is recognized, the ambient light compensation may be turned off temporarily. This ambient light compensation involves subtracting the light measured when the light source is turned off from the light measured when the light source is turned on. By turning off the ambient light compensation, the optical calibration signal becomes directly visible in the PPG signal.

Thus, a calibration signal can be detected by a sensor while its light source is turned on if there is no ambient light compensation. For example, if a calibration signal is detected during a period with the light source turned off, the ambient light compensation may then be turned off so that the calibration signal can continue to be detected while the light source is turned on. Alternatively, a suitably chosen calibration signal may be used, for example one which has different calibration signal levels during the light on and off periods. This can be achieved using a random noise signal or a sinusoidal calibration signal.

If the calibration signal is instead analyzed only during periods when the light source is turned off, then the issue of possible cancellation of the calibration signal by ambient light compensation is avoided.

The examples above make use of two calibration signals, one sent from the first PPG sensor to the second, and the other sent from the second PPG sensor to the first. However, in a more basic implementation, only one sensor (e.g. the second PPG sensor) provides a calibration signal to the other (e.g. the first PPG sensor). The second PPG sensor may then mark in its own data (e.g. in a memory or in the streamed data) the time at which it sent out the calibration signal, or else it may detect its own optical signal at the same time.

In this way, a marker can be set in the data of the second PPG sensor to mark the time at which the calibration signal is sent out (at the start of the calibration signal, or at a recognizable point in the calibration signal, or at any point during or before or after the calibration signal but with a known timing with respect to the calibration signal).

If there is no optical coupling between the second PPG sensor and its own signal, the marker may be used instead of a second optical calibration signal. As mentioned above, another option (instead of marking its own data or receiving a second calibration signal from the first sensor) is that the second PPG sensor can detect its own optical calibration signal as well for example in the manner explained with reference to FIG. 5. An acknowledgement signal may also be sent by the first PPG sensor to acknowledge that it has received the calibration signal. This may be an optical signal or could be sent e.g. via Bluetooth.

An acknowledgement signal acknowledging that the calibration signal has been received may be provided. Such an acknowledgement could however also be done by wireless communication such as using Bluetooth.

The monitoring system may also be for monitoring detection of a second optical calibration signal, wherein the second optical calibration signal is for detection by the second PPG sensor and is generated by the first light source.

The second optical calibration signal for example also functions as an acknowledgement signal.

The examples above are based on a cross coupling approach. This invention relates to a self-coupling approach.

Figures 7, 8:
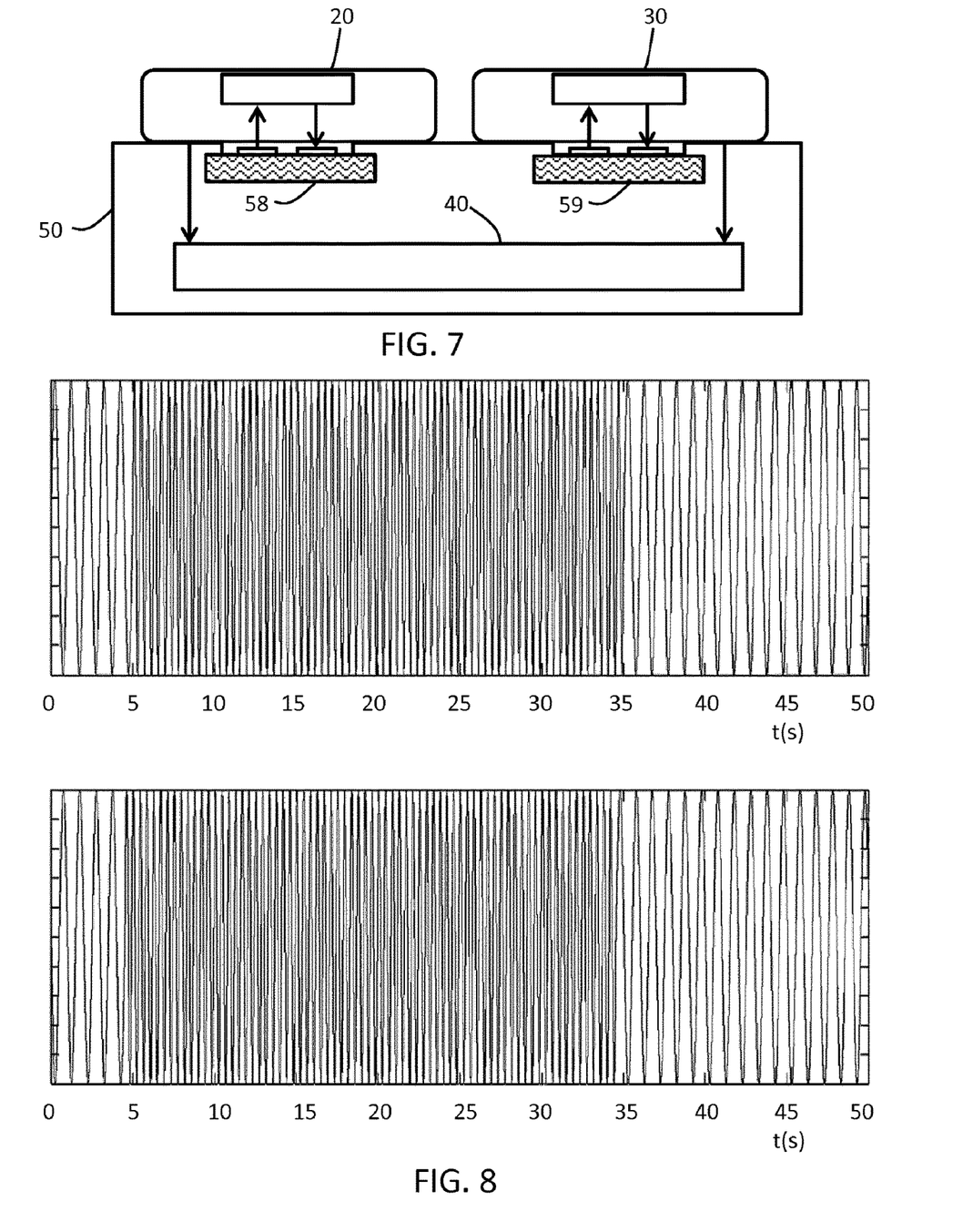
FIG. 7 shows a fifth example of a sensor arrangement using multiple PPG sensors.
FIG. 8 shows timing diagrams for a synchronization signal received at two PPG sensors at the same time, but with different clock domains.

FIG. 7 shows an example in which the PPG sensors are again placed onto a docking station 50, but rather than connecting the optical pathways as in the examples above the devices are placed such that they are each facing a controllable reflector. The first PPG sensor 20 faces a first reflector 58 and the second PPG sensor 30 faces a second reflector 59. They may be regions of a single device. The reflectors (or single reflector) have a controllable reflectivity over time. An advantage of this approach is that it enables the most basic sensor PPG to be used without adaptation. The sensor measurements can be made when the light source is turned on.

The reflector may be implemented using a passive-matrix LCD display for example. By varying the reflectivity of the display over time, the amount of light reflected from the light source to the light detector will also vary. By doing this to both PPG sensors at the same time, the time offset between the recorded signals can be detected. In particular, the received signal provides a measure of the absolute time period since a common event (which is the absolute time at which the reflectivity starts being controlled).

Control of the reflection results in generation of the calibration signals.

The nature of the reflection function can be determined from the detected signal, so that absolute timing information can then be allocated to the detected signals.

In this example, a first optical coupling is between the first light source and the first optical detector and a second optical coupling is between the second light source and the second optical detector. Thus, instead of cross coupling the two PPG sensors together, the detector of each PPG sensor is used to detect the light output from the light source of that same PPG sensor.

By enabling timing calibration in the manner explained above, pulse delay measurement is possible. The optional controller 40 as shown in FIG. 2 may provide a pulse delay output 42.

Another approach is to provide a light source which provides a synchronization pulse sequence to both PPG sensors. The detection of this known pulse sequence in the recorded traces again enables the relative timing to be determined. In particular, the start and/or end of the known pulse sequence can be identified on the clock domain of each PPG sensor.

This concept can be applied using the same structure shown in FIG. 7. The units 58 and 59 are then implemented as light sources delivering synchronized pulse sequences, or else as a single shared light source. The pair of PPG sensors may be docked for synchronization measurement before and after capturing a set of data, so that the time offset and offset drift may be calculated.

The waveforms of FIG. 3 are simplified for the purposes of explaining the underlying principles. In practice, the low sampling frequency of a typical PPG sensor will not allow a direct (human) measurement of the time delay to the required accuracy. Instead, signal processing is need to derive the time delay to the desired level of accuracy, which is typically of the order of ones of milliseconds.

FIG. 8 shows two traces of signal amplitude versus time. Each has approximately 5 seconds of normal signal at the beginning, followed by a 30 second period of a 2.4 Hz sync pulse, and approximately 15 seconds of normal signal at the end. The signals are measured using a sampling frequency of 256 Hz.

For the purposes of explanation, the bottom plot has been selected to lag the first plot by 474.6 ms (486 samples at 1024 Hz sampling frequency). This approximate 0.5 s lag can be seen when looking at the raw plots, but of course the lag cannot be manually determined more accurately.

Figure 9:
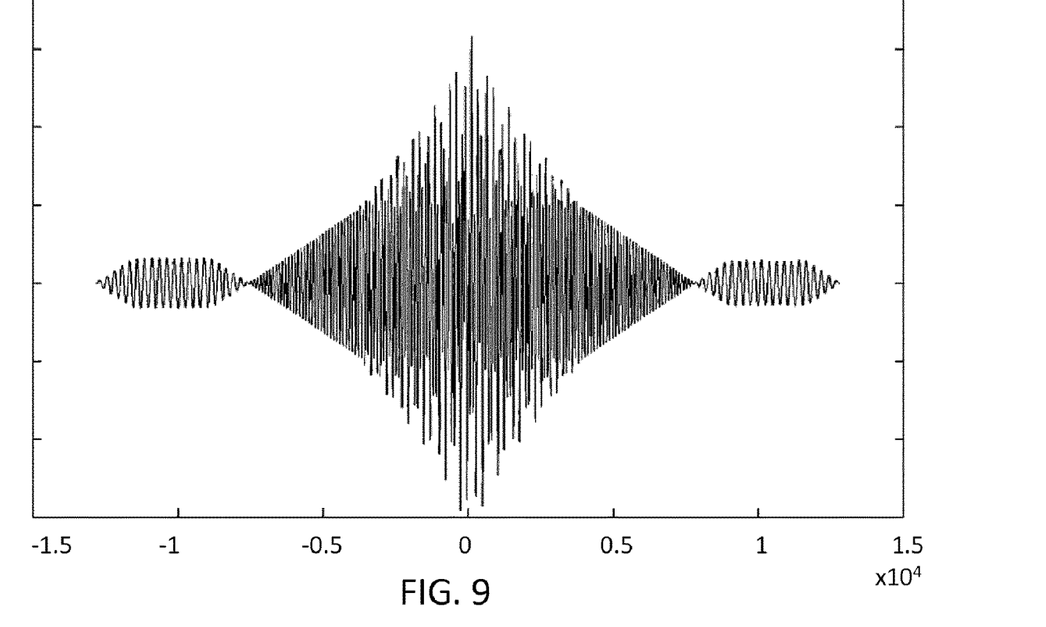
FIG. 9 shows a cross correlation of the signals of FIG. 8.

FIG. 9 shows a cross correlation of the two signals, which plots the cross correlation versus the selected delay between them. It is centered about zero delay.

Figure 10:
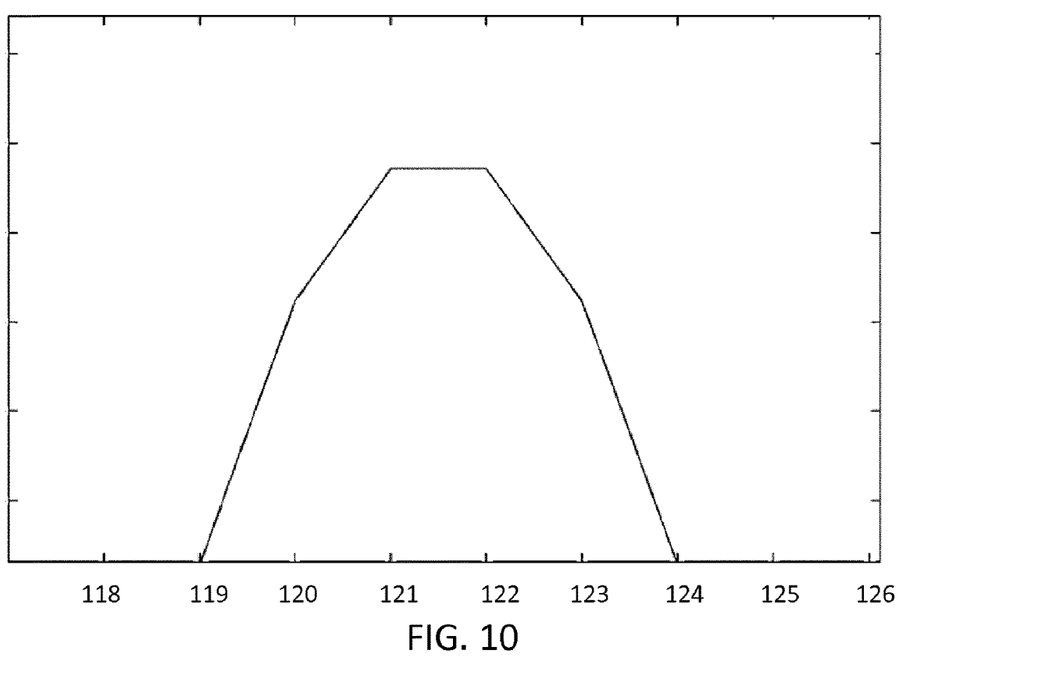
FIG. 10 shows a zoomed in part of the cross correlation signal of FIG. 9.

FIG. 10 shows the same cross correlation function, but shows the peak of the function in enlarged form, with the cross correlation value versus the delay expressed as a number of samples (i.e. the sample difference used to calculate the function). It indicates that the peak is at either 121 or 122 samples delay (472.7 or 476.6 ms at Fs=256 Hz). Thus, it can be seen that the cross correlation function enables the delay to be determined to millisecond accuracy.

Figure 11:
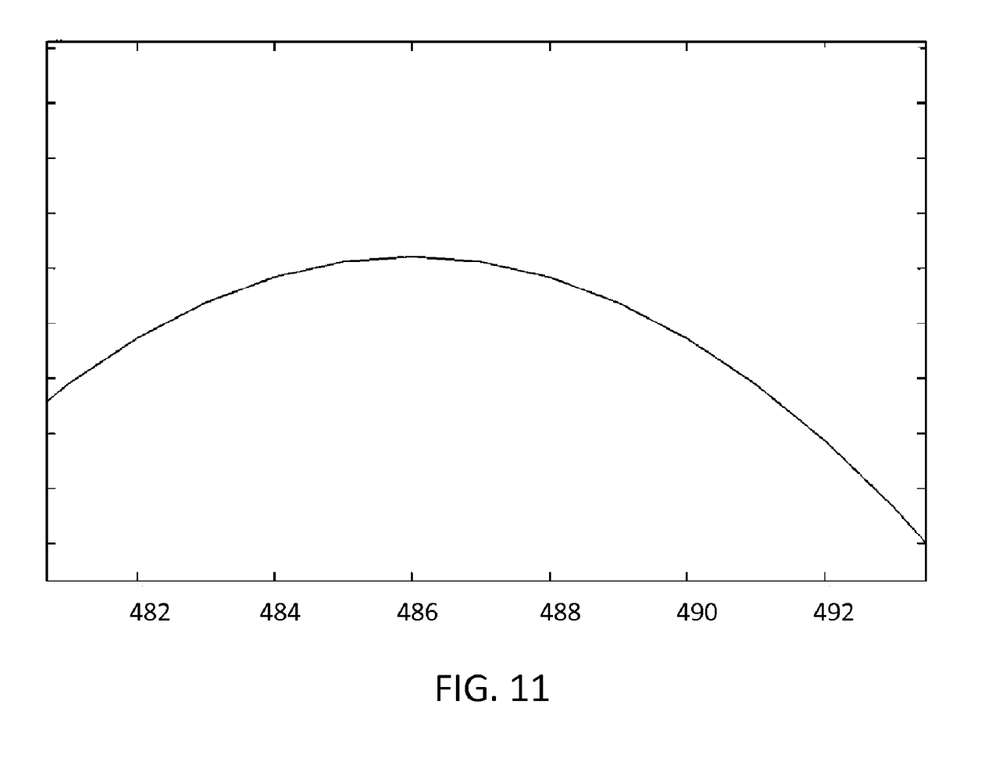
FIG. 11 shows a zoomed in part of the cross correlation signal of FIG. 9 after up-sampling.

FIG. 11 shows the same cross correlation peak as FIG. 10, but after first up-sampling the two input signals to 1024 Hz sample frequency. The peak is now at exactly 486 samples delay, or 474.6 ms (at Fs=1024 Hz).

As well as up-sampling the input signals it is possible to first take the cross-correlation of the two low sample rate signals, and then up-sample the resultant. The output will be the same.

Other signal processing approaches may be employed. Thus, any known approach for processing a pair of signals with near identical content but time-shifted can be used which enables the time shift to be extracted.

This cross correlation approach may be used in all examples above, including the reflection version, in which a known amplitude function is present in the two signals but with a time shift. It will now be understood that the pulse sequences shown schematically in FIG. 3 may in practice comprise a signal of known frequency for a particular duration, but they may also comprise a particular pulse sequence or amplitude function.

A further feature which may be used is to synchronize the device with a device measuring an electrical signal such as ECG. The electrical signal modulating the optical couplings in the example of FIG. 6 may for example be output directly to positive and negative leads of an ECG device (or scaled to form a suitable output within the signal range of the ECG device such as a maximum 8 mV peak-peak signal). In this way, a calibration signal will also show up in the ECG signal, at the same time as in the optical signals. This can be very useful if not only pulse delay is to be measured, but also pulse arrival time (PAT).

The example of FIG. 6 makes use of a controlled reflectance. However, other modulation approaches may be used, such as a controlled transmittance. This may be of interest for a transmissive PPG sensor, for example based on two finger clips which may be clipped on opposite sides of a docking station (in this case a rod) which could change its transmission properties in order to implement the calibration signal. The changed optical coupling may be implemented using liquid crystals, so again using display technologies.

The calibration (i.e. the extraction of the time lag) may be implemented by a computer program which forms or is part of the controller 40. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

The examples above are based on synchronizing two PPG sensors. However, the same approach may be used for synchronizing the signals from more than two sensors. For example a set of three or more sensors may be daisy-chained using a docking station, or else there may be three or more of the controllable reflectors.

Furthermore, the examples above are based on monitoring synchronization signals at both PPG sensors. There may be only one optical synchronization signal that needs to be monitored. For example, a button may be pressed on the first PPG sensor to send out a light pattern to be detected by the second optical detector (of the second PPG sensor) for calibration purposes. It is not then necessary to make the second PPG sensor also send out a light pattern to be detected by the first optical sensor. A time stamp can be inserted into the data captured by the first optical detector at the moment the button is pressed. This time stamp then serves as the time calibration of the first PPG sensor, to be matched with the detected calibration light pattern as measured by the photodetector of the second PPG sensor. This approach can also take into account a known delay between pressing the button and sending out the light pattern.

Essentially, what is needed is an identifiable signal in each detector trace in which the relative absolute time difference between those two identifiable signals is known. The various examples given above provide examples of how to implement this.

A calibration at the start of a measuring cycle may synchronize the clocks, but by performing a second calibration at the end of a measurement period (say 8 hours overnight) any relative drift can also be compensated.

As explained above, the invention enables the two PPG traces to be synchronized with respect to each other. This involves placing time markers in both traces. By matching these time markers from the two devices, the time base of the two devices can then be aligned with respect to offset and drift between the two independent clocks. This involves for example shifting the time axis of one trace and/or stretching the time axis.

For offset and drift correction between the clocks of the two devices, at least two of those marker pairs are present and a relative shift and scaling of the time axes takes place. With a single marker pair, correction for offset is possible which involves only a shift of the time axes relative to each other.

The examples above enable PD to be determined. There are other possible measurements based on multiple PPG measurements, such as arterial stiffness. The invention is not limited to these two examples, and is applicable whenever multiple PPG signals need to be synchronized.

The PPG sensors may for example make use of a camera flash as the optical source, and a camera image sensor as the sensor device. In this way, with a suitable application running on a mobile phone, a PPG sensor and PD sensor can be implemented.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. A sensor system, comprising:
    a first PPG sensor having a first light source a first optical detector and a first processor with a first clock domain;
    a second PPG sensor having a second light source a second optical detector and a second processor with a second clock domain;
    a docking station, which provides a first optical coupling between the first light source and the first optical detector and a second optical coupling between the second light source and the second optical detector;
    a monitoring system adapted to monitor detection of first and second optical calibration signals, wherein the first optical calibration signal is adapted to be detected by the first optical detector of the first PPG sensor and is generated by the first optical coupling and the second optical calibration signal is adapted to be detected by the second optical detector of the second PPG sensor and is generated by the second optical coupling,
    wherein the monitoring system is adapted to perform time calibration between the first and second clock domains of the first and second PPG sensors by determining a time offset between the detected signals.

2. A system as claimed in claim 1, wherein the first and second optical couplings have an optical reflectance or transmittance function with known absolute timing relationship.

3. A system as claimed in claim 2, wherein the first and second optical couplings each comprise a reflector with a reflection characteristic which is varied over time.

4. A system as claimed in claim 3, wherein the reflectors comprise a display device such as an LCD display.

5. A system as claimed in claim 4, wherein the reflectors together form a common display device.

6. A system as claimed in claim 2, wherein the first and second optical couplings each comprise structure with a transmission characteristic which is adapted to be controlled over time.

7. A pulse delay measurement device, comprising:
    a sensor system as claimed in any preceding claim; and
    a controller for obtaining PPG signals from the first and second PPG sensors, and deriving a pulse delay using the time calibration.

8. A sensor calibration method for calibrating first and second PPG sensors, the first PPG sensor having a first light source a first optical detector and a first processor with a first clock domain and the second PPG sensor having a second light source a second optical detector and a second processor with a second clock domain, the method comprising:
    placing the first and second PPG sensors on a docking station, which provides a first optical coupling between the first light source and the first optical detector and a second optical coupling between the second light source and the second optical detector,
    generating a first optical calibration signal using the optical coupling and generating a second optical calibration signal using the second optical coupling by controlling the first and second optical couplings with known absolute timing relationship; and
    performing time calibration between the first and second clock domains of the first and second PPG sensors by determining a time offset between detected signals at the first and second optical detectors.

9. A pulse delay sensing method comprising:
    performing sensing calibration using the method as claimed in claim 8; and
    after the sensing calibration, obtaining PPG signals from the first and second PPG sensors, and deriving a pulse delay.

10. A computer program product comprising computer program code means which is adapted, when run on a computer which forms part of the system of claim 1.

* * * * *